United States Patent [19]
Rupp et al.

[11] Patent Number: 5,210,037
[45] Date of Patent: May 11, 1993

[54] METHOD TO ENHANCE TPA PRODUCTION

[75] Inventors: Randall G. Rupp, La Honda; John C. Lane, Foster City, both of Calif.

[73] Assignee: Centocor Incorporated, Malvern, Pa.

[21] Appl. No.: 474,651

[22] Filed: Feb. 2, 1990

Related U.S. Application Data

[63] Continuation of Ser. No. 171,666, Mar. 22, 1988, abandoned.

[51] Int. Cl.$^5$ .......................... C12N 9/64; C12N 5/10
[52] U.S. Cl. .................................. 435/226; 435/240.3; 435/240.31
[58] Field of Search ............. 435/212, 219, 226, 240.3, 435/240.31

[56] References Cited

U.S. PATENT DOCUMENTS 4,751,084  6/1988  Feder et al. .................... 435/212 X

FOREIGN PATENT DOCUMENTS 0041766  12/1981  European Pat. Off. ............ 435/226
0093619  11/1983  European Pat. Off. ......... 435/172.3
0225440  7/1985   German Democratic Rep. ................... 435/240.3
2104081  3/1983   United Kingdom ............. 435/240.3
2181741  4/1987   United Kingdom ............. 435/240.2

OTHER PUBLICATIONS

Chang, *Biochim. Biophys. Acta* (1986) 823:161–194.
Graham, *J. Gen. Virol.* (1977) 36:56–72.
Moyer, *In Vitro Cellular and Developmental Biology* (1977) 23:141–146.
Rhim, *Science* (1985) 227:1250–1252.
*Difco Manual, Dehydrated Culture Media and Reagents for Microbiology*, Tenth Ed., pp. 160–164 and 1000, 1984.

*Primary Examiner*—Charles L. Patterson, Jr.
*Attorney, Agent, or Firm*—Morrison & Foerster

[57] ABSTRACT

A medium supplement which promotes the secretion of tPA from cells producing this protein natively or by virtue of recombinant transformation without the concomitant addition of contaminating proteins is described. Autoclaved brain/heart infusion preparations contribute virtually no extraneous proteins to the medium but greatly enhance the secretion of tPA.

8 Claims, 4 Drawing Sheets

PA.1 powder monitored at 280nm

PA.1 powder monitored at 254 nm

Autoclaved/280 nm

Autoclaved/254 nm

METHOD TO ENHANCE TPA PRODUCTION

This application is a continuation of application Ser. No. 07/171,666, filed Mar. 22, 1988.

TECHNICAL FIELD

The invention relates to the field of protein production using mammalian cell culture. In particular, it relates to a method to enhance production of a specific protein, tPA, from mammalian cells by adjustment of medium conditions.

BACKGROUND ART

Tissue plasminogen activator (tPA) can be prepared by culturing cells which produce it, either on a large or small scale. The cells may produce tPA either natively, or by virtue of transformation with the recombinant gene. The colon fibroblast cell line, CCD18Co, isolated from the colon mucosa of a neonate, is available from the ATCC as accession no. CRL1459. This strain is known to produce tissue plasminogen activator as its normal cellular product. Various techniques are available for extending the life of these normally tPA-secreting cells. See, for example, Chang, S. E., *Biochem Biophys Acts* (1986) 823:161-194; Rhim, J. S., *Science* (1985) 227:1250-1252; Graham, F. L., *J Gen Virol* (1977) 36:59-72; Moyer, M. P., *In Vitro Cellular and Developmental Biology* (1987) 23:141-146.

In addition, mammalian cell lines, such as murine and Chinese hamster ovary cells, have been transfected with vectors bearing expression systems for tPA and obtained as stable transformed lines capable of producing this protein. See, for example, published EPO applications 117,059 and 117,060.

Methods are also available for culture of mammalian cells on a practical scale. Particularly advantageous is the use of a static maintenance reactor corresponding to that described in U.S. Pat. No. 4,537,860. Other techniques for culturing mammalian cells include use of beads for anchorage dependent cells, utilization of large-scale fermenters, roller bottles, and various perfusion reactors.

It is generally found that the levels of tPA produced by recombinantly modified mammalian cells are much higher than those obtained from cells which produce this protein normally. To some extent, the levels of tPA obtained are dependent on the nature of the culture medium, and it has been considered advantageous to supplement basal medium with serum. Even this supplementation, however, does not increase the level of production from non-recombinant cells to that obtainable using recombinant cells; also, it creates problems with respect to purifying the tPA product away from the serum proteins. The present invention suggests a culture medium which permits high levels of production of tPA both by recombinant and native producers.

DISCLOSURE OF THE INVENTION

It has now been found that the addition of a supplement to basal medium which supplement is a mixture of mammalian brain and heart infusions, a composition commonly used in bacterial fermentations, dramatically increases the levels of tPA produced by both recombinant and native tPA-producing cells. Addition of this supplement to the basal medium permits the deletion of the serum additive, and greatly increases the efficiency of desired protein production.

In one aspect, the invention is directed to a method to enhance tPA production by mammalian cells in culture, which method comprises culturing cells capable of producing tPA in a medium which contains a brain/heart infusion (BHI) preparation which is equivalent in effect to that obtained by adding about 0.2-2% (w/v) of a reference composition (PA.1) containing approximately 200 grams of calf brain infusion and 250 grams of beef heart infusion, in addition to minor amounts of additional components.

In another aspect, the invention is directed to a cell culture containing the BHI-supplemented medium according to the method of the invention and cells capable of producing tPA.

MODES OF CARRYING OUT THE INVENTION

Figure 1A:
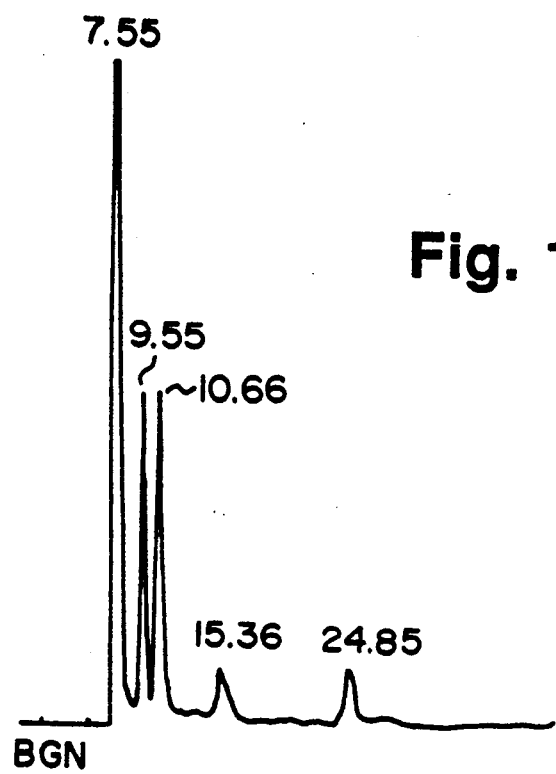
FIGS. 1A and 1B represent ion-pairing HPLC profiles of PA.1 with and without autoclaving.

The invention rests on the discovery that supplementation of mammalian cell culture medium with brain/heart infusion results in a marked increase in tPA production. As used herein, brain/heart infusion refers to a mixture of solids which are derived by infusion of mammalian brain and heart. Commercial preparations, designated BHI, are available, and commonly include mixtures of calf brain infusion products and beef heart infusion products with their various additives, such as protease, peptide, dextrose, salts, and so forth. As used herein, "BHI" is defined as any comparable material which contains in major amount the products of infusion of mammalian brain and mammalian heart.

A typical commercially available preparation, designated herein PA.1, for example, contains 200 grams calf brain infusion, 250, grams beef heart infusion, 10 grams proteose peptone, 2 grams dextrose, 5 grams sodium chloride, and 2.5 grams disodium phosphate. Other formulations of appropriate infusion products can also be substituted.

When used in the method of the invention, the brain/heart infusion preparation is supplied to the medium in a weight/volume percentage which corresponds to that of a percentage in the range of 0.2-2% when the above-exemplified commercial BHI preparation (PA.1) is used. Of course, different actual percentages can be supplied, depending on the composition of the added preparation. For example, if the BHI preparation contains smaller amounts of the essential ingredients in comparison to the supplementary materials, larger percentages need to be used. Therefore, "a percentage of BHI equivalent to 0.2-2% (w/v) of PA.1" refers to a supplementation with a BHI preparation which gives a comparable stimulation in tPA production to that exhibited by this range of PA.1. It is understood that use of infusion derived from other mammals, e.g., porcine or ovine brain or heart, could be substituted, but that the required amounts would need to be adjusted to achieve equivalence with the bovine-derived supplements.

Suitable basal media to which the BHI may be added include a variety of culture media known to support the growth of mammalian cells. Many such media are commercially available, such as HAM'S F-12, DMEM, and RPMI-1640. Other basal media may also be used.

According to the method of the invention, the cells are grown in basal medium to a cell density of about $2-4\times10^4$ cells/cm$^2$. The use of a perfusion system rather than a batch culture medium is preferred. When the cell density has reached the desired level, the perfusing medium is supplemented with BHI in an amount equivalent to that provided by 0.2-2% (w/v) of PA.1. Culturing is continued, and tPA is harvested from the conditioned medium by any suitable means known in the art. Preferred is the direct and continuous harvest of tPA from the medium perfused through the culture, in particular by a purification procedure disclosed and claimed in U.S. Ser. No. 092,502, filed Sep. 3, 1987, assigned to the same assignee and incorporated herein by reference.

It is preferred that the BHI preparation be autoclaved prior to the addition of the culture medium, since the essential components are apparently stable to this process, and infectious agents such as viruses are destroyed. Accordingly, in a preferred process of the invention, the BHI preparation is subjected to autoclave pressures and temperatures of 15 psi and 121° C. for a suitable period of time, e.g., 20-30 minutes, before use to supplement the medium.

It also, preferred that the BHI preparation be characterized prior to use. Since the preparation is by definition a mixture of components derived by extraction from mammalian tissues, a certain degree of variability is to be expected, depending on the specific source and the infusion techniques used. Effective BHI preparations are typified by that exemplified as PA.1 herein. Example 1 below shows the characteristics of this particular BHI preparation.

The cells which produce tPA are innoculated into suitable culture medium depending on the nature of the cells selected. Basically, two types of tPA-producing cells may be used — recombinantly transformed mammalian cells such as Chinese hamster ovary (CHO) cells which have been transfected with vectors containing the tPA gene under control of, for example, the SV40 promoter, or cells which produce tPA without genetic alteration. These latter, native tPA producing cells, may also be modified to extend their life in vitro culture. The nature of the inoculum and the nature of the growth medium are, of course, interrelated, and a suitable medium is selected for the cell line being utilized.

In one conventional protocol, the cell cultures are grown to confluence in ordinary tissue culture flasks and then transferred to roller bottles or large scale reactors such as fermenters or perfusion reactors, including the above mentioned static maintenance reactor system. The cells are grown to the desired cell density, of the order of about $2-4\times10^4$ cells/cm$^2$ and the supplementing amount of BHI is then added. The mode of addition depends, of course, on the nature of the reactor; in a perfusion system the supplementation is made to the medium flowing through the perfusion system; in a fermenter the supplement is simply added to the medium. The culture is further maintained for a suitable period to produce tPA; this tPA-producing period depending, of course, also on the nature of the reactor system. Fermenter and roller bottle systems are essentially batch processes; whereas the cells can be maintained for longer periods in perfusion reactors and the tPA harvested during the culturing.

The tPA produced can be monitored and recovered and purified according to means known in the art, including that disclosed in U.S. Ser. No. 092,502 (supra), filed on even date herewith, and incorporated herein by reference.

The following examples are intended to illustrate the invention, but not to limit its scope.

EXAMPLE 1

Characterization of PA.1

Powdered PA.1 was reconstituted to 5 mg/ml in HPLC-grade water. Autoclaved material was supplied as a 50% (w/v) solution, and was diluted to 5 mg/ml in HPLC-grade water.

Total Protein: Total protein was run using the Bradford microtiter plate method. Briefly, samples were diluted in tenfold series in HPLC water. Forty microliters of each dilution and of undiluted samples were loaded, in duplicate, into designated wells of an Immulon-II 96-well plate. Forty ul standards (0, 5, 10, 20, 40, 50, 60 and 80 ug/ml) prepared from BSA (Sigma, RIA-Grade) were also added in duplicate to the appropriate wells. One hundred sixty ul of Bradford reagent was dispensed into each well and the plate incubated for 10 minutes at ambient temperature. The plate was read on the Bio-Rad EIZ Reader at 600 nm and data processed with the corresponding software.

Total protein for freshly prepared PA.1 was 2.5 ug/ml and autoclaved material was 4.9 ug/ml. Since both samples were at a concentration of 5 mg/ml total solids, this translates into a percent protein of 0.05% and 0.1% for the fresh and autoclaved material, respectively.

Electrophoresis: An equivalent of 500 ug, dry weight, of each sample was mixed with 0.5 volume of 3×SDS-PAGE reducing buffer and boiled for 10 minutes. These were then loaded into wells at each end of a 5-20% linear gradient SDS-PAGE such that they could be analyzed both by was cut in half and processed with silver reagent and Coomassie using standard procedures.

Peptides of approximately 2,000-4,000 apparent molecular weight or larger are routinely retained and detected on such gels when present; however, none was found. Considering that a 500 ug equivalent of total solids was loaded, this would mean that any retained peptide would comprise <0.0005% of the total solids assuming a 2-3 ng/band detectability with silver staining.

Ion-Pairing Chromatography: Samples were analyzed by ion-pairing chromatography using a Bio-Rad HPX-87H resin designed to separate monosaccharides, disaccharides, and tricarboxylic acid cycle intermediates. One hundred ul injections of undiluted samples were made, eluted with 0.01 NH$_2$SO$_4$ with a flow rate of 0.6 ml/min, and detected by refractive index. Run time was 40 minutes with a 10 minutes wash; chart speed was set at 3, attenuation at 128, peak width at 4, and A and B sensitivity at 10,000 and 10, respectively; the results are shown in FIGS. 1A and 1B for unautoclaved and autoclaved PA.1 respectively at 5 mg/ml.

Figure 1B:
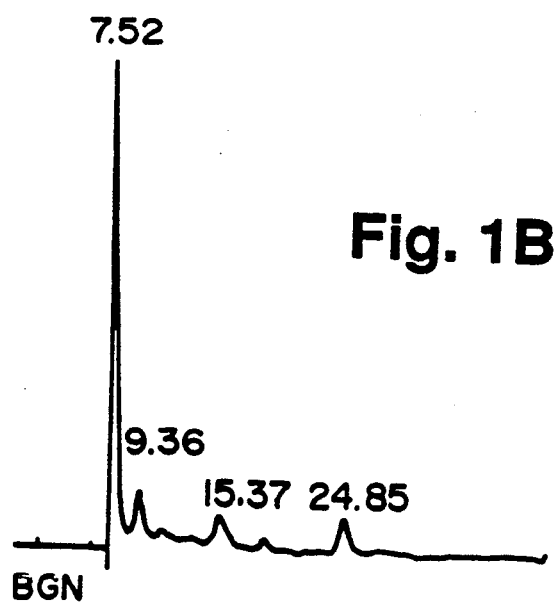
Figure 2A:
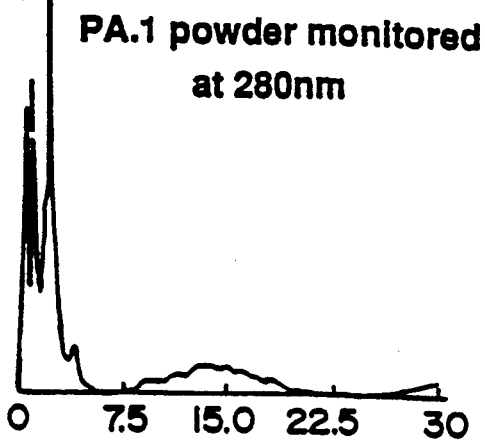
FIGS. 2A-2D represent elution profiles on reverse-phase HPLC of autoclaved and unautoclaved PA.1 monitored at 245 nm and 280 nm.
Figure 2B:
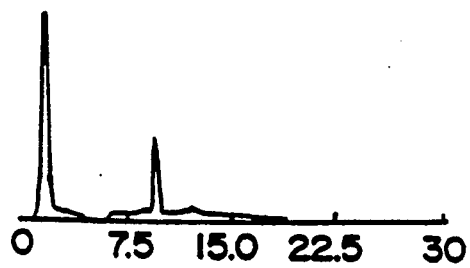
Figure 2C:
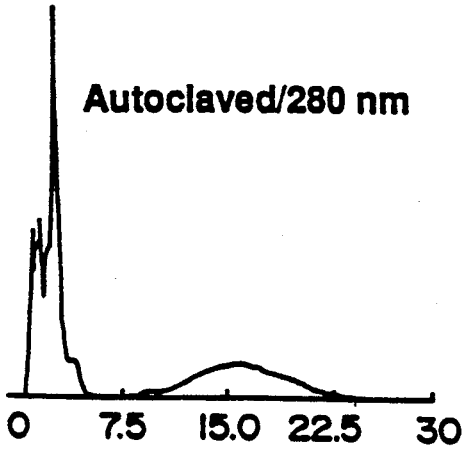
Figure 2D:
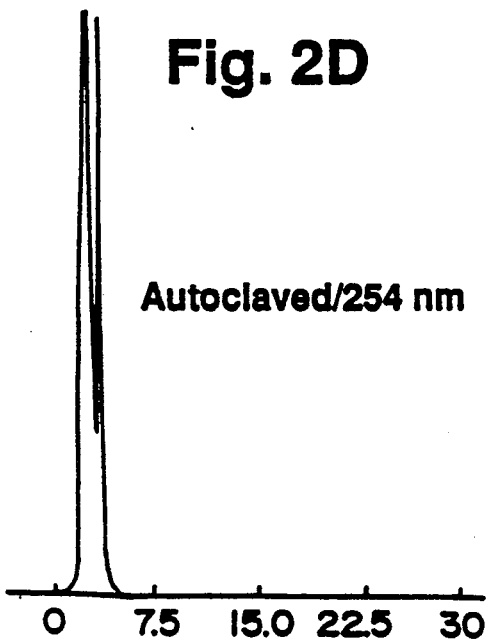

FIGS. 1A and 1B represent "fingerprints" of the PA.1 and related materials. It is obvious that changes in structural integrity take place when the material is autoclaved, as evidenced by the loss of peaks at 9.36-9.55 and 10.66 minutes retention time. The material eluting at 10.66 minutes is known to be glucose. That eluting at 15.36 minutes is believed to be lactic acid. The peak at 24.85 minutes elutes in the area of acetate, while the peak at 9.36–9.55 minutes elutes near sucrose.

Amino Acid Analysis: Samples were analyzed for their amino acid content both prior to and following hydrolysis (110° C., 24 hours, vapor phase). Two and one-half and 25 ug equivalents were analyzed in all instances. Amino acids were derivatized with PITC and analyzed by ODS/reverse-phase chromatography.

Table 1 shows the difference in fresh and peptide-bound amino acids upon hydrolysis of PA.1.

TABLE 1

Amino Acid Analysis of Freshly Prepared and Hydrolyzed PA.1 (nmoles)

| Amino Acid | Fresh (non-hydrolyzed) | Fresh (hydrolyzed) | Autoclaved (non-hydrolyzed) | Autoclaved (hydrolyzed) |
|---|---|---|---|---|
| Asp | 266.0 | 1422.6 | 163.2 | 1081.3 |
| Glu | 239.1 | 4100.7 | 116.9 | 2965.9 |
| Ser | 251.2 | 1527.9 | 177.6 | 1043.7 |
| Gly | 218.0 | 3417.0 | 138.5 | 2430.6 |
| His | 118.0 | 386.0 | 46.8 | 258.7 |
| Arg | 341.3 | 1040.6 | 182.7 | 686.6 |
| Thr | 250.5 | 1065.1 | 137.5 | 763.0 |
| Ala | 384.0 | 2181.0 | 258.5 | 1622.6 |
| Pro | 152.0 | 3117.1 | 118.7 | 2674.9 |
| Tyr | 197.3 | 200.3 | 176.9 | * |
| Val | 418.9 | 638.9 | 176.0 | * |
| Met | 236.1 | 11.6 | 17.9 | * |
| Cys | 37.7 | 908.7 | 7.5 | * |
| Ile | 230.2 | 36.2 | ND | * |
| Leu | 1146.7 | 77.8 | 497.6 | * |
| Phe | 542.8 | ND | ND | * |
| Lys | 3999.9 | 1831.6 | 1666.3 | * |

ND = None detected
*Retention times were shifted such that accurate determinations were not possible.

The increase in amino acids upon hydrolysis suggests, as suspected, that PA.1 consists of a variety of low molecular weight peptides in addition to free amino acids; a large percentage of amino acids generated by hydrolysis are polar.

Reverse Phase Chromatography: 200 ul of each sample (5 mg/ml) was injected and analyzed by reverse phase chromatography using gradient elution. The gradient was 0–100% solution B in solution A over 30 min with a flow rate of 1 ml/min where solution A was 0.1% (W/B) tFA in water and solvent B was 60% (V/V) $CH_3CN$ in solvent A. Elution was monitored at both 280 nm and 254 nm. These results are shown in FIGS. 2A–2D.

These results also constitute a fingerprint based upon the differential polarities of respective components of PA.1. When monitored at 280 nm (FIGS. 2A and 2C for fresh and autoclaved PA.1 respectively), there is a general elution of material ranging from polar to nonpolar, the exact nature of which is unknown. When monitored at 254 nm, (FIGS. 2B and 2D) the nonpolar components appear to be significantly reduced upon autoclaving.

Figure 3A:
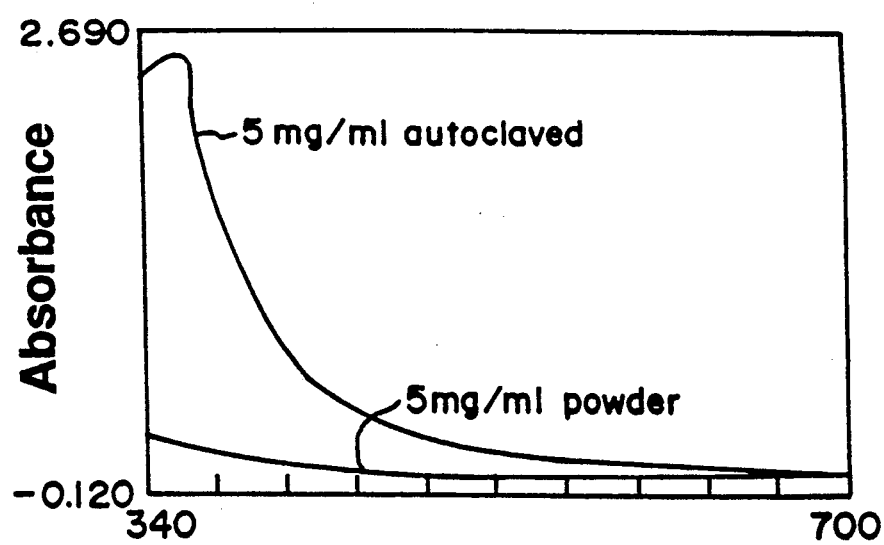
FIGS. 3A and 3B represent the visible and UV spectra of PA.1 with and without autoclaving.
Figure 3B:
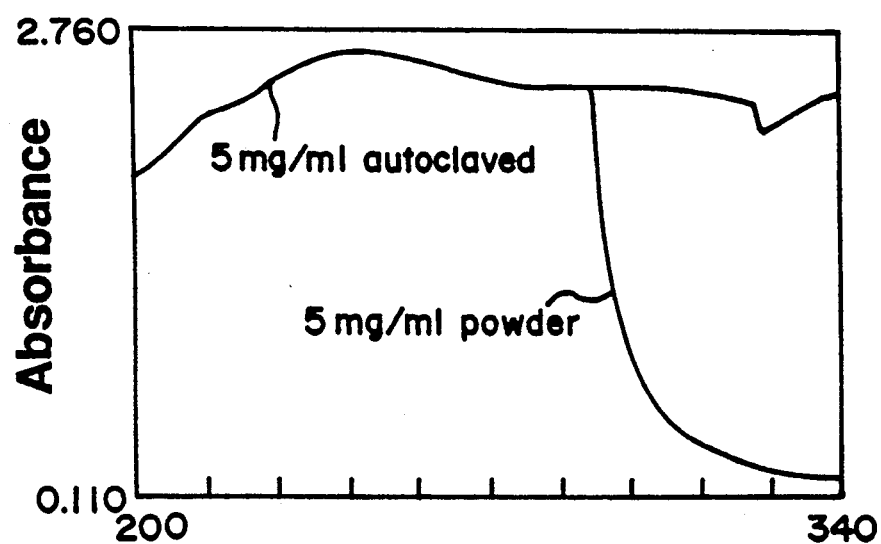

Absorbance Profile: Absorbance profiles in the UV-visible show an apparent structural difference between freshly prepared and autoclaved material as indicated by the observed spectral shift (FIGS. 3A and 3B). The freshly prepared material gives an absorbance profile indicative of a mixture of UV-absorbing amino acids (tryptophan, tyrosine and phenylalanine), low molecular weight peptides, and, perhaps, amino sugars. The decreased absorbance in the far UV indicates the absence of high molecular weight biomolecules, such as nucleic acids, oligosaccharides, glycolipids, etc.

EXAMPLE 2

Effect of PA.1 on tPA Production

SV40-transformed human colon cells (ATCC accession no. CRL 1459 transformed with SV40 vectors to extend their life) were grown to confluence in each of three 25-$cm^2$ tissue culture flasks.

On day 0, samples were taken from each flask for tPA analysis, and the remaining medium from each flask was discarded. Each flask was then rinsed with 2 ml PBS followed by 2 ml experimental medium and then 7 ml of experimental medium was added to each flask. Over the course of the study, samples were drawn from the flasks for tPA analysis and the remaining medium from each flask was discarded, the flask rinsed with 2 ml experimental medium and 7 ml of experimental medium was added. These changes were done at intervals of 24–48 hours.

The experimental media were BA-M (basal medium BA-M.0), FBS-containing medium (BA-M.0 +5% FBS), and the supplemented medium of the invention, BA-M.0 +0.5% PA.1 +1 ug/ml insulin +5 ug/ml transferrin (BA-M.4). PA.1 was prepared as a 10% stock solution and autoclaved at 121° C. for 30 minutes before addition to BA-M.0 to obtain BA-M.4.

Figure 4:
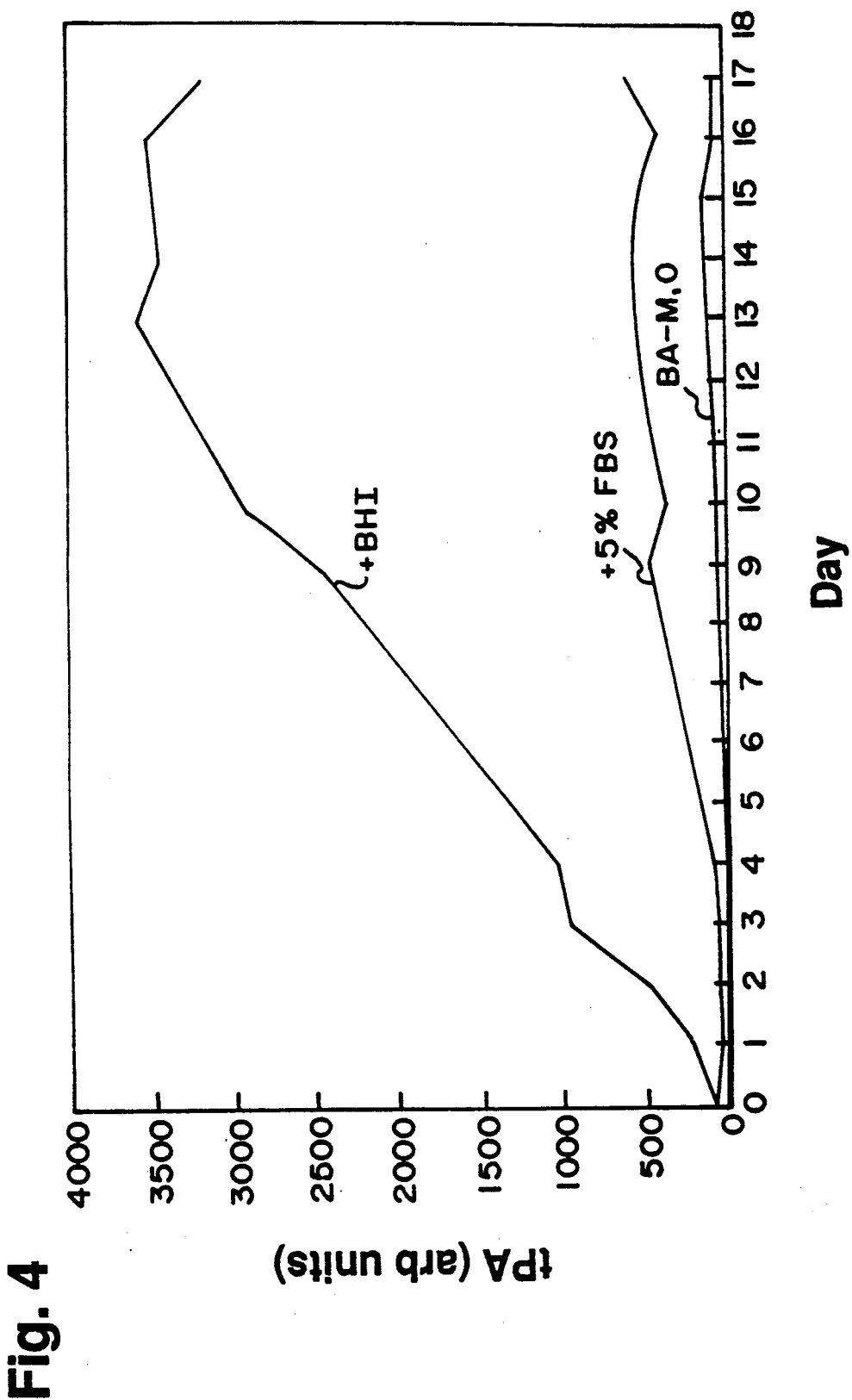
FIG. 4 is a graphical representation of the effect of BHI addition on tPA production by human colon fibroblast cells.

The results of this study are shown in FIG. 4. By day 12, tPA in serum-free medium with 0.5% PA.1 contained tPA at 3,600 arbitrary units; cells in the medium supplemented with serum contained only 450 units. Unsupplemented medium produced almost no tPA.

Additional determinations using basal media with and without additions of BHI and serum are summarized in Table 2. The SV40-immortalized cells were incubated and sampled as described above, and gave the results shown in Table 2.

TABLE 2

| | tPA (ng/ml) Days in Culture | | | | |
|---|---|---|---|---|---|
| | 1 | 2 | 3 | 4 | 6 |
| BA-M.4 + 0.1% BSA | 17 | 15 | 20 | 39 | 86 |
| BA-M.4 + 0.1% BSA (without PA.1) | 9 | 13 | 12 | 26 | 39 |
| BA-M.6 | 6 | 15 | 20 | 20 | 28 |
| BA-M.6 (without PA.1) | 9 | 8 | 7 | 7 | 3 |
| BA-M.0 + 5% FBS | 18 | 14 | 20 | 29 | 44 |

As shown in the table, BA-M.4 was supplemented with 0.1% BSA and was tested with and without 0.5% (wt/v) autoclaved PA.1. As shown in Table 2, cells cultured in the presence of medium with autoclaved PA.1 produced approximately twice as much tPA as those incubated in its absence.

An additional basal medium, BA-M.6 (BA-M.0 with 1 ug/ml insulin, 5 ug/ml transferrin, 0.3% "Excyte" lipid mixture, 0.02% BSA, and 0.5% (wt/v) autoclaved PA.1) was tested as such and without PA.1.

As shown in the table, cells incubated in this basal medium (with PA.1) produce almost 10 times as much tPA as those incubated in medium which does not contain this.

To some extent, BHI can be replaced with 5% fetal bovine serum, as shown in the last row of the table. However, serum supplementation carries the serious disadvantage of causing difficulties in purification of the tPA produced. As described above, the BHI is virtually protein free.

We claim:

1. A method to improve production of tissue plasmiogen activator (tPA) in a culture of a tPA-producing cell line which tPA-producing cell line is a transformed mammalian cell line that produces tPA by virtue of a recombinant expression system, which method comprises culturing said transformed cell line capable of producing tPA in a basal medium which is specifically suitable for said cell line wherein said basal medium further contains an amount of a preparation of brain/heart infusion (BHI) effective to improve tPA production by said cell line.

2. The method of claim 1 wherein the BHI is supplied in amount equivalent to 0.2-2% (wt/v) PA.1.

3. The method of claim 2 wherein the BHI is supplied as 0.2-2% PA.1.

4. The method of claim 3 wherein the BHI is supplied as 0.5% PA.1.

5. A cell culture comprising a mammalian cell line capable of secreting tissue plasminogen activator (tPA) wherein said cell line is a transformed mammalian cell line that normally produces tPA or that produces tPA by virtue of a recombinant expression system, and a basal medium which is specifically suitable for said cell line and which further contains an amount of a preparation of brain-heart infusion (BHI) effective to improve tPA production by said cell line.

6. The culture of claim 5 wherein the BHI is supplied as 0.2-2% (wt/v) PA.1.

7. The culture of claim 5 wherein the BHI is supplied as 0.5% PA.1.

8. The culture of claim 5 wherein the cell line is ATCC CRL1459.

* * * * *